United States Patent

Franke et al.

[11] Patent Number: 5,118,685
[45] Date of Patent: Jun. 2, 1992

[54] AMINOPROPANOL DERIVATIVES OF SUBSTITUTED 2-HYDROXY-PROPIOPHENONES, AND THERAPEUTIC AGENTS CONTAINING THESE COMPOUNDS

[75] Inventors: Albrecht Franke, Wachenheim; Wolfgang Spiegler, Worms; Hardo Siegel, Speyer; Claus D. Mueller, Viernheim; Gerda von Philipsborn, Weinheim; Dieter Lenke, Ludwigshafen; Josef Gries, Wachenheim, all of Fed. Rep. of Germany

[73] Assignee: BASF Aktiengesellschaft, Ludwigshafen, Fed. Rep. of Germany

[21] Appl. No.: 677,307

[22] Filed: Dec. 3, 1984

[30] Foreign Application Priority Data

Dec. 2, 1983 [DE] Fed. Rep. of Germany ....... 3343671

[51] Int. Cl.$^5$ .................. A61K 31/40; A61K 31/535; C07D 403/10
[52] U.S. Cl. .................. 514/235.5; 514/326; 514/331; 514/427; 514/406; 514/252; 514/235.8; 546/208; 546/211; 546/232; 544/371; 544/399; 544/366; 544/140; 544/141; 544/173; 548/378; 548/562
[58] Field of Search ............ 546/334, 194, 212, 211, 546/214; 544/360, 374, 371, 372, 124, 140, 146, 141, 152; 548/561, 356; 549/496, 76; 514/232, 237, 255, 318, 326, 357, 406, 427, 438, 471

[56] References Cited

U.S. PATENT DOCUMENTS 3,723,476 3/1973 Nakanishi et al. ............... 546/334

FOREIGN PATENT DOCUMENTS 2001431 7/1971 Fed. Rep. of Germany .......... 32/21
3133814 3/1983 Fed. Rep. of Germany .......... 93/06
3226863 4/1983 Fed. Rep. of Germany .......... 97/10
1307455 2/1973 United Kingdom ................... 97/10
2103600 2/1983 United Kingdom ................. 546/334

Primary Examiner—Jane T. Fan
Attorney, Agent, or Firm—Keil & Weinkauf

[57] ABSTRACT

Aminopropanol derivatives of the formula:

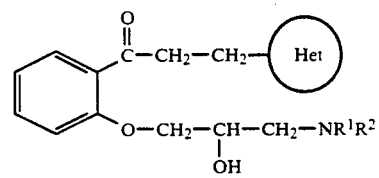

where $R^1$ and $R^2$ are identical or different and are each hydrogen, alkyl, cycloalkyl, alkenyl, alkynyl or hydroxyalkyl, each of not more than 6 carbon atoms, alkoxyalkyl, alkylthioalkyl or dialkylaminoalkyl, each of not more than 9 carbon atoms in total, or phenylalkyl or phenoxyalkyl where the alkyl radical is of not more than 6 carbon atoms and the phenyl radical is unsubstituted or substituted by alkyl or alkoxy, each of not more than 3 carbon atoms, or $R^1$ and $R^2$, together with the nitrogen atom which links them, form a 5-membered to 7-membered saturated heterocyclic ring which can be substituted by one or two phenyl and/or hydroxyl radicals and can contain an oxygen or nitrogen atom, as a further heteroatom in the ring, and such an additional nitrogen atom can be substituted by alkyl of 1 to 3 carbon atoms or by phenyl, and —Het is thien-2-yl, thien-3-yl, pyrid-2-yl, pyrid-3-yl, pyrid-4-yl, fur-2-yl, 1-alkylpyrr-2-yl, 1-alkylpyrr-3-yl or 1-alkylpyrazol-4-yl, alkyl being of 1 to 3 carbon atoms, and their physiologically tolerated addition salts with acids, and antiarrhythmic agents containing these compounds.

3 Claims, No Drawings

AMINOPROPANOL DERIVATIVES OF SUBSTITUTED 2-HYDROXY-PROPIOPHENONES, AND THERAPEUTIC AGENTS CONTAINING THESE COMPOUNDS

The present invention relates to novel aminopropanol derivatives of β-substituted 2-hydroxypropiophenones, a process for their preparation, and therapeutic agents which contain these compounds and can be used as antiarrhythmic agents.

German Laid-Open Applications DOS 2,001,431, DOS 3,133,814 and DOS 3,226,863 disclose that the aminopropanol derivatives of 2-hydroxy-β-phenyl-propiophenone possess antiarrhythmic activity. This applies in particular to 2-(2'-hydroxy-3'-n-propylamino-propoxy)-β-phenylpropiophenone hydrochloride, which is the known antiarrhythmic agent propafenone.

It is an object of the present invention to provide antiarrhythmic agents which, after oral administration, are more effective than the above compound.

We have found that this object is achieved, and that aminopropanol derivatives of the formula I

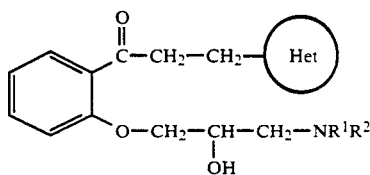

I where $R^1$ and $R^2$ are identical or different and are each hydrogen, alkyl, cycloalkyl, alkenyl, alkynyl or hydroxyalkyl, each of not more than 6 carbon atoms, alkoxyalkyl, alkylthioalkyl or dialkylaminoalkyl, each of not more than 9 carbon atoms in total, or phenylalkyl or phenoxyalkyl where the alkyl radical is of not more than 6 carbon atoms and the phenyl radical is unsubstituted or substituted by alkyl or alkoxy, each of not more than 3 carbon atoms, or $R^1$ and $R^2$, together with the nitrogen atom which links them, form a 5-membered to 7-membered saturated heterocyclic ring which can be substituted by one or two phenyl and/or hydroxyl radicals and can contain an oxygen or nitrogen atom as a further heteroatom in the ring, and such an additional nitrogen atom can be substituted by alkyl of 1 to 3 carbon atoms or by phenyl, and —Het is thien-2-yl, thien-3-yl, pyrid-2-yl, pyrid-3-yl, pyrid-4-yl, fur-2-yl, 1-alkyl-pyrr-2-yl, 1-alkylpyrr-3-yl or 1-alkylpyrazol-4-yl, alkyl being of 1 to 3 carbon atoms, and their physiologically tolerated addition salts with acids possess useful pharmacological properties.

Particularly noteworthy compounds of the formula I are those in which the group $NR^1R^2$ is a piperidine, piperazine, N-methylpiperazine, morpholine or diisopropylamino radical, and those in which $R^1$ and/or $R^2$ are hydrogen, propyl, butyl, pentyl, alkoxyalkyl or hydroxyalkyl, e.g. n-propyl, isopropyl, n-butyl, isobutyl, tert.-butyl, n-pentyl, sec.-pentyl, isopentyl, neopentyl, β-methoxyethyl and β-hydroxyethyl. Particularly preferred heterocyclic radicals are pyridyl, 1-methyl-pyrr-2-yl, 1-methylpyrr-3-yl and 1-methylpyrazol-4-yl.

Examples of compounds in addition to those stated in the Examples are:

2-(2'-hydroxy-3'-isopropylaminopropoxy)-β-(thien-2-yl)-propiophenone,
2-(2'-hydroxy-3'-n-pentylaminopropoxy)-β-(thien-2-yl)-propiophenone,
2-[2'-hydroxy-3'-(2-methoxyethylamino)-propoxy]-β-(thien-2-yl)-propiophenone,
2-(2'-hydroxy-3'-n-propylaminopropoxy)-β-(thien-3-yl)propiophenone,
2-[2'-hydroxy-3'-(2-hydroxyethylamino)-propoxy]-β-(thien-3-yl)-propiophenone,
2-[2'-hydroxy-3'-(2,2-dimethylpropylamino)-propoxy]-β-(thien-3-yl)-propiophenone,
2-(2'-hydroxy-3'-n-propylaminopropoxy)-β-(pyrid-2-yl)-propiophenone,
2-(2'-hydroxy-3'-n-propylaminopropoxy)-β-(pyrid-4-yl)-propiophenone,
2-(2'-hydroxy-3'-tert.-butylaminopropoxy)-β-(fur-2-yl)-propiophenone,
2-[2'-hydroxy-3'-(2-(3,4-dimethoxyphenyl)-ethylamino)-propoxy]-β-(fur-2-yl)-propiophenone,
2-[2'-hydroxy-3'-(2-dimethylaminoethylamino)-propoxy]-β-[1-methylpyrr-2-yl]-propiophenone,
2-[2'-hydroxy-3'-(4-methylpiperazin-1-yl)-propoxy]-β-[1-methylpyrr-2-yl]-propiophenone,
2-(2'-hydroxy-3'-piperidinopropoxy)-β-[1-methylpyrr-2-yl]-propiophenone,
2-[2'-hydroxy-3'-(but-1-yn-3-ylamino)-propoxy]-β-[1-methylpyrr-2-yl]-propiophenone,
2-[2'-hydroxy-3'-[4-(2-methoxyphenyl)-piperazin-1-yl]-propoxy-β-[1-methylpyrr-3-yl)]-propiophenone,
2-(2'-hydroxy-3'-morpholinopropoxy)-β-[1-methyl-pyrazol-4-yl]-propiophenone,
2-[2'-hydroxy-3'-(4-methylpiperazin-1-yl)-propoxy]-β-[1-methylpyrazol-4-yl]-propiophenone,
2-(2'-hydroxy-3'-allylaminopropoxy)-β-[1-methyl-pyrazol-4-yl]-propiophenone,
2-[2'-hydroxy-3'-(3-dimethylaminopropylamino)-propoxy]-β-]1-methylpyrazol-4-yl]-propiophenone,
2-[2'-hydroxy-3'-(4-hydroxy-4-phenylpiperidino)-propoxy]-β-[1-methylpyrazol-4-yl]-propiophenone,
2-(2'-hydroxy-3'-aminopropoxy)-β-[1-methylpyrazol-4-yl]-propiophenone,
2-(2'-hydroxy-3'-methylaminopropoxy)-β-[1-methyl-pyrazol-4-yl]-propiophenone,
2-(2'-hydroxy-3'-cyclohexylaminopropoxy)-β-[1-methylpyrazol-4-yl]-propiophenone and
2-[2'-hydroxy-3'-(2-(3,4-dimethoxyphenyl)-ethylamino)-propoxy]-β-[1-methylpyrazol-4-yl]-propiophenone.

The compounds according to the invention can be prepared by a method in which a) a compound of the formula

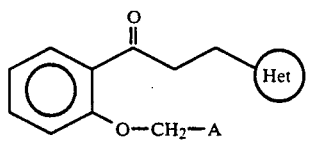

II where A is

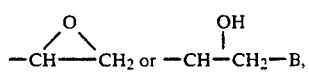

in which B is a nucleofugic leaving group is reacted with an amine of the formula

HNR¹R²  III where R¹ and R² have the stated meanings, or b) a compound of the formula IV

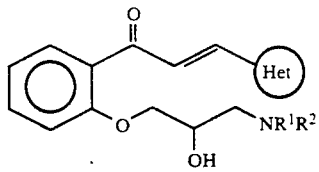

where R¹ and R² have the stated meanings, is hydrogenated catalytically, and, if desired, the resulting compound is converted to its addition salts with physiologically tolerated acids.

In the case of process a), the leaving group B is preferably a halogen atom, in particular a chlorine, bromine or iodine atom. Other examples of suitable nucleofugic leaving groups are aromatic or aliphatic sulfonic acid radicals, such as the p-toluenesulfonic acid or methanesulfonic acid radical.

The reactions are carried out at room temperature or elevated temperatures, advantageously at from 50° to 120° C., and under atmospheric pressure or in a closed vessel under superatmospheric pressure, if necessary with heating to the stated temperature.

The starting compounds can be reacted directly, i.e. without the addition of a diluent or solvent. Advantageously, however, the reactions are carried out in the presence of an inert diluent or solvent, for example a lower alcohol of 1 to 4 carbon atoms, such as methanol, ethanol or propanol, preferably isopropanol or ethanol, a lower saturated dialkyl ether, dialkyl glycol ether or cyclic ether, such as diethyl ether, 1,2-dimethoxyethane, tetrahydrofuran or dioxane, benzene or an alkylbenzene, such as toluene or xylene, an aliphatic hydrocarbon, such as hexane, heptane or octane, a lower aliphatic ketone, such as acetone, methyl ethyl ketone or methyl isobutyl ketone, a dialkylformamide, such as dimethylformamide or diethylformamide, or dimethyl sulfoxide, or in the presence of water, or in a mixture of the stated solvents. The amine of the general formula HNR¹R², used in excess, can, if desired, also be used as a diluent or solvent.

Preferred solvents in the reaction of the compound II

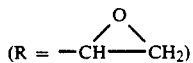

with an amine HNR¹R² are lower alcohols, in particular e or isopropanol, the reaction preferably being carried out at from 50° to 120° C. and under atmospheric pressure.

The reaction is completed in general in the course of from 2 to 15 hours, depending on the reaction temperature. The reaction product can be isolated in a conventional manner, for example by filtration or by distilling off the diluent or solvent from the reaction mixture. The compound obtained is purified in a conventional manner, for example by recrystallization from a solvent, by conversion to an addition compound with an acid, or by column chromatography.

Some of the starting compounds of the general formula II are known. Those which are unknown can be prepared as follows:

o-Hydroxyacetophenone is condensed with a heterocyclic aldehyde to give the α,β-unsaturated ketone by a conventional method, as described in, for example, Org. Reactions, Volume 16, page 1 et seq., John Wiley Publishers, New York, 1968; Houben-Weyl, Methoden der organischen Chemie, Volume 7/2b, page 1457 et seq., G. Thieme Verlag, Stuttgart, 1976; or Chem. Ber. 94 (1961), 26. These ketones are hydrogenated catalytically to the corresponding β-substituted 2-hydroxypropiophenones, likewise by a conventional method, as described in, for example, R. N. Rylander, "Catalytic Hydrogenation over Pt-Metals", page 282, Academic Press, 1967.

These β-substituted 2-hydroxypropiophenones are converted to the propiophenones of the formula II by alkylation with an epihalohydrin or with a 1,3-dihalopropan-2-ol by a conventional method.

Suitable epihalohydrins are epichlorohydrin, epibromohydrin and epiiodohydrin, while particularly suitable 1,3-dihalopropan-2-ols are 1,3-dichloropropan-2-ol and 1,3-dibromopropan-2-ol.

The reactions of the β-substituted 2-hydroxypropiophenones for the preparation of the compounds of the formula II are carried out at from 50° to 80° C. and under atmospheric or superatmospheric pressure, in an inert diluent or solvent, e.g. acetone, methanol or dimethylformamide, in the presence of a base, such as potassium carbonate, as an acid acceptor.

Some of the β-substituted 2-hydroxypropiophenones and some of the starting compounds II can be employed directly in the subsequent reaction steps without prior purification.

Process b) takes place readily in alcoholic solution. Particularly useful catalysts are noble metal catalysts, such as palladium, on carbon.

The novel compounds of the formula I possess a center of chirality at carbon atom 2 of the aliphatic side chain, and are obtained as racemates, which can be separated into the optically active antipodes by a conventional method, for example by formation of diastereomer salts with optically active acids, such as dibenzoyltartaric acid, camphor-10-sulfonic acid, ditoluyltartaric acid or 3-bromocamphor-β-sulfonic acid.

If desired, the resulting compounds according to the invention are converted to the addition salts with physiologically tolerated acids. Examples of suitable conventional physiologically tolerated acids are hydrochloric acid, hydrobromic acid, phosphoric acid and sulfuric acid (as inorganic acids), and oxalic acid, maleic acid, fumaric acid, lactic acid, tartaric acid, malic acid, citric acid, salicylic acid, adipic acid and benzoic acid (as organic acids). Other suitable acids are described in Fortschritte der Arzneimittelforschung, Volume 10, pages 224–225, Birkhäuser Verlag, Basel and Stuttgart, 1966.

As a rule, the addition salts with acids are obtained in a conventional manner by mixing the free base or a solution of this with the appropriate acid or a solution of this in an organic solvent, for example a lower alcohol, such as methanol, ethanol or propanol, or a lower ketone, such as acetone, methyl ethyl ketone or methyl isobutyl ketone, or an ether, such as diethyl ether, tetrahydrofuran or dioxane. To improve the deposition of crystals, mixtures of the stated solvents can also be used. Moreover, pharmaceutically acceptable aqueous solutions of acid addition compounds of the aminopropanol derivatives of the formula I can be prepared by dissolving the free base in an aqueous solution of the acid.

The novel compounds and their physiologically tolerated addition salts with acids possess antiarrhythmic, β-sympatholytic and Ca antagonistic properties and are therefore particularly suitable for the pharmacotherapy of cardiac arrhythmias, for the prophylaxis of sudden heart death, and for the treatment of coronary diseases of the heart. Their effectiveness after oral administration is substantially superior to that of the active compound propafenone.

The present invention accordingly also relates to therapeutic agents or formulations which, in addition to conventional pharmaceutical carriers and diluents, contain, as the active compound, a compound of the formula I or one of its physiologically tolerated addition salts with acids.

The therapeutic agents or formulations are prepared in a conventional manner by compounding an appropriate dose with the conventional carriers or diluents and the conventional pharmaceutical auxiliaries, in accordance with the desired route of administration (cf. R. Voigt, Lehrbuch der pharmazeutischen Technologie, VEB-Verlag Volk und Gesundheit, Berlin, 1975). Suitable single therapeutic doses are doses of from 1 to 500, preferably from 5 to 100, mg.

The preferred formulations are those suitable for oral administration. Examples of these are tablets, film tablets, coated tablets, capsules, pills, powders, solutions or suspensions, or forms which exert a depot effect.

Of course, formulations for parenteral administration, e.g. injection solutions, are also suitable. Suppositories are a further example of suitable formulations.

For practical use, the compounds employed according to the invention are formulated with the carriers conventionally used in pharmaceutical production. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, e.g. corn starch, alginic acid or polyvinylpyrrolidone, binders, e.g. starch or gelatine, lubricants, e.g. magnesium stearate or talc, and/or agents for achieving a depot effect, e.g. carboxypolymethylene, carboxymethylcellulose, cellulose acetate phthalate or polyvinyl acetate. The tablets can also consist of a plurality of layers.

Correspondingly, coated tablets can be prepared by coating cores, prepared similarly to the tablets, with agents conventionally used in tablet coatings, for example polyvinylpyrrolidone or shellac, gum arabic, talc, titanium dioxide or sugar. The coating can also consist of a plurality of layers, and the auxiliaries mentioned above in connection with tablets may be used therein.

Solutions or suspensions containing the novel active compounds may additionally contain flavor improvers, such as saccharin, cyclamates or sugar, and, for example, aromas, such as vanilline or orange extract. They can also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatine capsules.

Suitable suppositories can be prepared, for example, by mixing the active compounds with appropriate carriers, such as neutral fats or polyethylene glycol or their derivatives.

The Examples which follow illustrate the invention.

A) Preparation of the Starting Compounds

EXAMPLE I

3-Oxo-1-(thien-2-yl)-3-(2'-hydroxyphenyl)-propene 20.4 g of o-hydroxyacetophenone and 16.8 g of 2iophenecarbaldehyde were added to a mixture of 150 g of ethanol and 20 g of NaOH in 100 ml of $H_2O$ at room temperature, and the thoroughly stirred reaction mixture was brought to 50° C. in the course of 60 minutes and then cooled, after which it was neutralized with 2 N HCl with thorough cooling. The resulting precipitate was filtered off under suction, washed thoroughly with $H_2O$ and then recrystallized from acetone/$H_2O$. 24.5 g (71% yield) of yellow crystals of melting point 98° C. were obtained.

The following compounds were prepared by a similar method:

3-oxo-1-(fur-2-yl)-3-(2'-hydroxyphenyl)-propene, m.p. 106° C.;

3-oxo-1-(pyrid-3-yl)-3-(2'-hydroxyphenyl)-propene, m.p. 152° C.;

3-oxo-1-[1-methylpyrr-2-yl]-3-(2'-hydroxyphenyl)-propene, m.p. 80°-84° C.;

3-oxo-1-[1-methylpyrr-3-yl]-3-(2'-hydroxyphenyl)-propene, m.p. 117°-120° C.; and 3-oxo-1-[1-methylpyrazol-4-yl]-3-(2'-hydroxyphenyl)-propene, m.p. 152° C.

EXAMPLE II

2-Hydroxy-β-(thien-2-yl)-propiophenone 8 g of 3-oxo-1-(thien-2-yl)-3-(2'-hydroxyphenyl)-propene were dissolved in 200 ml of methanol, and hydrogenated in the presence of a Raney nickel catalyst at from 40° to 50° C. under atmospheric pressure. Absorption of hydrogen was complete after about 4 hours. The mixture was cooled, the catalyst was filtered off and the solvent was distilled off under reduced pressure to give 7.6 g (95% yield) of a colorless oily residue, which crystallized on prolonged standing (m.p. 38°-42° C.)

The following compounds were prepared by a similar method:

2-hydroxy-β-(fur-2-yl)-propiophenone, oily;

2-hydroxy-β-(pyrid-3-yl)-propiophenone, m.p. 68°-73° C., 2-hydroxy-β-[1-methylpyrr-2-yl]-propiophenone, oily;

2-hydroxy-β-[1-methylpyrr-3-yl]-propiophenone, m.p. 44°-45° C.; and 2-hydroxy-β-[1-methylpyrazol-4-yl]-propiophenone, m.p. 74°-79° C.,

EXAMPLE III 2-(2',3'-Epoxypropoxy)-β-(thien-2-yl)-propiophenone 8.2 g of 2-hydroxy-β-(thien-2-yl)-propiophenone and 15.5 g of epichlorohydrin were stirred thoroughly in the presence of 10.7 g of anhydrous $K_2CO_3$ in 25 mL of dimethylformamide for 20 hours at 80° C. After the mixture had cooled, 150 ml of $H_2O$ were added, the mixture was extracted several times with ether, the combined ether extracts were dried with $Na_2SO_4$, and the solvent and excess epichlorohydrin were distilled off under reduced pressure to give 9.2 g (91.5% yield) of an oily residue, which was used without further purification.

All other glycidyl ethers were prepared by a similar method, and were used without further purification for the subsequent reaction.

EXAMPLE IV

2-[2'-Hydroxy-3'-(N-isopropyl-N-benzylamino)-propoxy]-acetophenone hydrochloride 20 g of 2-(2',3'-epoxypropoxy)-acetophenone were dissolved in 150 ml of isopropanol, and 16 ml of N-isopropyl-N-benzylamine were added. The mixture was refluxed for 8 hours and then cooled, after which the solvent was distilled off under reduced pressure, and the remaining residue was converted to the hydrochloride with a solution of hydrochloric acid in ether. Recrystallization from acetone/methanol/ether gave 25.1 g (64% yield) of a product of melting point 143°–146° C.

EXAMPLE V

3-Oxo-1-(pyrid-3-yl)-3-[2-(2'-hydroxy-3'-(N-isopropyl-N-benzylamino)-propoxy)-phenyl]-propene 10 g of 2-[2'-hydroxy-3'-(N-isopropyl-N-benzylamino)-propoxy]-acetophenone were dissolved in 300 ml of methanol, and condensed with 3.3 g of pyridine-3-carbaldehyde in the presence of 4 g of NaOH by heating at 45° C. for from 5 to 6 hours. The mixture was cooled, and then 500 ml of $H_2O$ were added, 8 g (64% yield) of yellow crystals of melting point 145° C. being obtained in this manner.

B) Preparation of the Compounds According to the Invention

EXAMPLE 1

2-(2'-Hydroxy-3'-n-propylaminopropoxy)-β-(thien-2-yl)propiophenone hydrochloride 8 g of 2-(2',3'-epoxypropoxy)-β-(thien-2-yl)-propiophenone and 9.5 g of n-propylamine were dissolved in 150 ml of isopropanol, and the solution was refluxed for 8 hours. After the solution had cooled, the solvent was distilled off under reduced pressure to give 10.3 g of an oily residue, which crystallized on prolonged standing. By using a solution of hydrochloric acid in ether and recrystallizing the product from acetone/methanol/ether, 3.5 g (35% yield) of the hydrochloride of melting point 163° C. were isolated.

The following compounds were prepared from the appropriate starting materials, using a method similar to that described in Example 1:

TABLE

| Example No. | Het | $NR^1R^2$ | M.p. [°C.] | Salt | Molecular weight | Empirical formula |
|---|---|---|---|---|---|---|
| 2 | (5-methyl-furan-2-yl) | NH-propyl | 150–155 | Hydrochloride | 367.5 | $C_{19}H_{26}ClNO_4$ |
| 3 | (1,5-dimethyl-pyrrol-2-yl) | NH-isopropyl | 103 | Free base | 344 | $C_{20}H_{28}N_2O_3$ |
| 4 | " | NH-propyl | 137–138 | Fumarate | 461 | $C_{24}H_{32}N_2O_7$ |
| 5 | " | N-diisopropyl | 118 | ½ Fumarate | 444 | $C_{25}H_{36}N_2O_5$ |
| 6 | (1-methyl-pyrrol-2-yl) | NH-propyl | 132 | Hydrochloride | 380.5 | $C_{20}H_{29}ClN_2O_3$ |
| 7 | " | NH-isopropyl | 151–153 | ½ Fumarate | 402 | $C_{22}H_{30}N_2O_5$ |
| 8 | " | NH-tert-butyl | 150–153 | ½ Fumarate | 416 | $C_{23}H_{32}N_2O_5$ |
| 9 | (1-methyl-pyrazol-3-yl) | NH-propyl | 122 | Hydrochloride | 381.5 | $C_{19}H_{28}ClN_3O_3$ |

TABLE-continued

| Example No. | Het | NR¹R² | M.p. [°C.] | Salt | Molecular weight | Empirical formula |
|---|---|---|---|---|---|---|
| 10 | " | NH—⟨ (isopropyl) | 122-125 | Hydrochloride | 381.5 | $C_{19}H_{28}ClN_3O_3$ |
| 11 | " | NH—⟨ (cyclopropyl) | 140-143 | Oxalate | 433 | $C_{21}H_{27}N_3O_7$ |
| 12 | " | NH—C(CH₃)₂— | 131 | Fumarate | 489 | $C_{25}H_{35}N_3O_7$ |
| 13 | " | NH—C(CH₃)₃ | 185-188 | Hydrochloride | 395.5 | $C_{20}H_{30}ClN_3O_3$ |
| 14 | " | piperidino | 122-125 | Hydrochloride | 408.5 | $C_{21}H_{30}ClN_3O_3$ |
| 15 | " | NH—CH(CH₃)—CH₂—OCH₃ | 72-76 | Fumarate | 491 | $C_{24}H_{33}N_3O_8$ |

EXAMPLE 16

2-(2'-Hydroxy-3'-isopropylaminopropoxy)-β-(pyrid-3-yl)-propiophenone oxalate 8 g of 3-oxo-1-(pyrid-3-yl)-3-[2-(2'-hydroxy-3'-(N-isopropyl-N-benzylamino)-propoxy)-phenylamin)-propoxy)-phenyl]-propene were dissolved in 150 ml of ethyl acetate, and hydrogenated in the presence of Raney nickel under atmospheric pressure at from 40° to 50° C. until absorption of hydrogen was complete (320 cm³). The catalyst was filtered off and the solvent was then distilled off under reduced pressure to give 8.1 g of colorless, oily 2-[2'-hydroxy-3'-(N-isopropyl-N-benzylamino)-propoxy]-β-(pyrid-3-yl)-propiophenone. Without further purification, this product was hydrogenated in 200 ml of ethanol in the presence of 0.8 g of a 10% strength Pd/C catalyst under atmospheric pressure at from 40° to 50° C. until absorption of $H_2$ was complete. The catalyst was filtered off, and the solvent was then distilled off under reduced pressure. The remaining residue was dissolved in acetone, and a solution of oxalic acid in ethanol was added. Addition of ether gave 2.5 g (26% yield) of crystals of melting point 92°-96° C.

C) Use

In the pharmacological investigations to determine the antiarrhythmic action, a comparison was made with the conventional antiarrhythmic agents propafenone (2-(2'-hydroxy-3'-n-propylaminopropoxy)-β-phenyl-propiophenone; German Laid-Open Application DOS 2,001,431) and diprafenone (2-[2-hydroxy-3-(1,1-dimethylpropylamino)-propoxy]-ω-phenylpropiophenone; German Laid-Open Application DOS 3,133,814), the investigations being carried out on dogs, because metabolization of propafenone in this animal species is similar to that in man (cf. HEGE, H. G. et al., European Journal of Drug Metabolism and Pharmacokinetics, 9 (1984), 41, and HEGE, H. G. et al., Arzneimittelforschung/Drug Research 9 (1984), 34.

Male or female mongrel dogs weighing 12-15 kg were used. The substances to be tested were administered orally, 40 minutes after induction of anesthesia using Na pentobarbital (30 mg/kg i.v.). Cardiac arrhythmias were induced by infusion of aconitine (5 μg per kg per min), the infusion beginning 60 minutes after administration of the substance. In the ECG of untreated animals, arrhythmias (loss or inversion of P, ventricular tachyarrhythmias) occurred after an average infusion time of 6.4±0.29 min.

When the substances according to the invention were administered in a dose of 10 mg/kg, the time which elapsed before arrhythmias appeared was prolonged. This prolongation was from twice (Example 4) to six times (Example 7) greater than that obtained in the case of propafenone and the equivalent compound diprafenone; the antiarrhythmic activity is higher (Table 1).

TABLE 1

Antiarrhythmic action on aconitine-induced arrythmia in the dog (10 mg/kg, oral administration)

| Ex. no. | Prolongation of aconitin infusion period (Δ%) |
|---|---|
| 9 | 154 |
| 3 | 85 |
| 12 | 137 |
| 4 | 70 |
| 5 | 85 |
| 7 | 193 |
| propafenone | 34 |
| diprafenone | 33 |

The substances were also tested with regard to their action on arrhythmias after coronary ligature. This method permits conclusions to be drawn as to the action on arrhythmias after infarct in man. Male and female beagle dogs weighing 9-15 kg were used. The ramus descendens of the left coronary artery was ligatured by a modified method of Harris (Circulation, 1, 1318-1328, 1950). Tachycardic, usually ventricular arrhythmias of various origins resulted which were detectable on the ECG, with P loss QRS deformation and T wave elevation. The measure for determining antiarrhythmic action was the frequency (%) of normal heart actions ascertained during a 100-minute control period at 5-minute intervals. Hearbeats had to be at most 29% of the normal during this control period before a substance was administered. After administration, the ECG was run, as in the control period, for 100 minutes at 5-minute intervals, and then for a further 200 minutes at 10-minute intervals.

As Table 2 shows, the substances according to the invention were more effective than propafenone and diprafenone in this model too. Thus, the compound of Example 9 inhibited arrhythmias to just as great an extent as propafenone, and to a far greater extent than diprafenone, at an oral dosage rate of about 5 times less. The compounds of Examples 5 and 7 were, at 10 mg/kg, more active than propafenone and diprafenone at the same rate.

TABLE 2

Antiarrhythmic action on arrhythmias after infarct in the conscious dog

| | Increase in normal heart actions | |
|---|---|---|
| | | Dose mg/kg |
| Ex. no. | % | 10.0 | 21.5 |
| 5 | — | 66 | — |
| 7 | — | 92 | — |
| 9 | 74 | — | — |
| propafenone | 5 | 40 | 70 |
| diprafenone | — | — | 43 |

Toxicity tests (i.p. administration) carried out on female NMRI mice weighing 24-28 g showed that lethal doses of the substances according to the invention were in the same order of magnitude as those of the comparative substances. An increase in effectiveness is thus not concomitant with a corresponding rise in toxicity (Table 3).

TABLE 3

| Lethal doses after single administration (i.p.) in mice | |
|---|---|
| Ex. no. | LD$_{50}$ (mg/kg*) |
| 9 | 31.6 |
| 3 | 68.1 |
| 12 | 68.1 |
| 4 | 46.4 |
| 5 | 68.1 |
| 7 | 46.4 |
| propafenone | 46.4 |
| diprafenone | 68.1 |

*approximate values

We claim:

1. An aminopropanol derivative of the formula

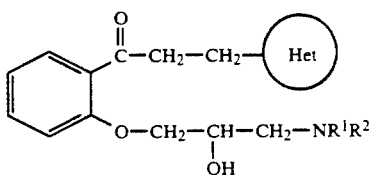

I where the group $NR^1R^2$ is a piperidine, piperazine, N-methylpiperazine, morpholine or diisopropylamino radical, or $R^1$ and $R^2$ are hydrogen, n-propyl, isopropyl, n-butyl, isobutyl, tert.-butyl, n-pentyl, sec.-pentyl, isopentyl, neopentyl, $\beta$-methoxy-alkyl or $\beta$-hydroxyalkyl of 2 or 3 carbon atoms or cycloalkyl of 3 to 6 carbon atoms and Het is, 1-alkylpyrr-2-yl, 1-alkylpyrr-3-yl or 1-alkylpyrazol-4-yl, alkyl being of 1 to 3 carbon atoms, and its physiologically tolerated addition salts with acids.

2. An aminopropanol derivative of the formula I as defined in claim 1, wherein the group HET is 1-methylpyrr-2-yl, 1-methylpyrr-3-yl or 1-methylpyrazol-4-yl.

3. An antiarrhythmic agent which contains, as the active ingredient, an effective amount of compound of the formula I as defined in claim 2, in addition to the conventional pharmaceutical auxiliaries and diluents.

* * * * *